(12) United States Patent
Kääriäinen et al.

(10) Patent No.: US 11,774,350 B2
(45) Date of Patent: Oct. 3, 2023

(54) METHOD AND APPARATUS FOR ANALYZING GASEOUS SAMPLES

(71) Applicant: Teknologian tutkimuskeskus VTT Oy, Espoo (FI)

(72) Inventors: Teemu Kääriäinen, VTT (FI); Albert Manninen, VTT (FI)

(73) Assignee: Teknologian tutkimuskeskus VTT Oy, Espoo (FI)

( * ) Notice: Subject to any disclaimer, the term of this patent is extended or adjusted under 35 U.S.C. 154(b) by 30 days.

(21) Appl. No.: 17/767,284

(22) PCT Filed: Oct. 8, 2020

(86) PCT No.: PCT/FI2020/050663
§ 371 (c)(1),
(2) Date: Apr. 7, 2022

(87) PCT Pub. No.: WO2021/069800
PCT Pub. Date: Apr. 15, 2021

(65) Prior Publication Data
US 2022/0364984 A1    Nov. 17, 2022

(30) Foreign Application Priority Data
Oct. 10, 2019    (FI) ........................................ 20195866

(51) Int. Cl.
*G01N 21/31*    (2006.01)
*G01N 21/25*    (2006.01)
(Continued)

(52) U.S. Cl.
CPC ....... *G01N 21/3103* (2013.01); *G01N 21/255* (2013.01); *G01N 21/39* (2013.01);
(Continued)

(58) Field of Classification Search
CPC .. G01N 21/3103; G01N 21/255; G01N 21/39; G01N 21/031; G01N 21/05;
(Continued)

(56) References Cited

U.S. PATENT DOCUMENTS 3,805,074 A * 4/1974 McCormack ...... G01N 21/3504
250/354.1
5,384,640 A   1/1995 Wong
(Continued)

FOREIGN PATENT DOCUMENTS

EP    0768521 A1    4/1997
EP    1022558 A2    7/2000
(Continued)

OTHER PUBLICATIONS

International Search Report, Application No. PCT/FI2020/050663, dated Dec. 18, 2020, 3 pages.
(Continued)

*Primary Examiner* — Tarifur R Chowdhury
*Assistant Examiner* — Carlos Perez-Guzman
(74) *Attorney, Agent, or Firm* — Ziegler IP Law Group (57) ABSTRACT

A measuring apparatus for measuring a spectrum of a gaseous sample includes
a tunable laser light source to provide an illuminating light beam,
a sample cell with an inner surface to provide scrambled light that is transmitted through the gaseous sample,
a detector to detect intensity of transmitted scrambled light and
a pressure control system to maintain an absolute pressure of the gaseous sample smaller than 50 kPa inside the sample cell to reduce spectral widths of spectral features of the gaseous sample. The measuring apparatus measures spectral transmittance values of the sample
(Continued)

by modulating the spectral position of the illuminating light, and detecting the intensity of the transmitted light at different spectral positions. The divergence of the illuminating light beam in a transverse direction is greater than 30° to cause multiple consecutive reflections of the scrambled light from the inner surface.

9 Claims, 8 Drawing Sheets

(51) Int. Cl.
*G01N 21/39* (2006.01)
*G01N 33/497* (2006.01)

(52) U.S. Cl.
CPC ... *G01N 33/497* (2013.01); *G01N 2021/3125* (2013.01); *G01N 2201/0221* (2013.01); *G01N 2201/0633* (2013.01)

(58) Field of Classification Search
CPC .............. G01N 21/0303; G01N 21/15; G01N 21/3504; G01N 33/497; G01N 2021/3125; G01N 2021/0378; G01N 2201/0221; G01N 2201/0633; G01N 2201/0631; G01J 2003/4334; G01J 3/0205; G01J 3/0291; G01J 3/0297; G01J 3/10; G01J 3/433
See application file for complete search history.

(56) References Cited

U.S. PATENT DOCUMENTS

| | | |
|---|---|---|
| 5,886,348 A | 3/1999 | Essure et al. |
| 6,091,504 A | 7/2000 | Walker et al. |
| 6,882,426 B1 | 4/2005 | Mueller |
| 2003/0202179 A1 | 10/2003 | Larsen et al. |
| 2004/0042006 A1* | 3/2004 | Chen .................... G01J 3/44 |
| | | 356/301 |
| 2008/0231857 A1* | 9/2008 | Depeursinge ...... G01N 33/4925 |
| | | 356/246 |
| 2008/0255769 A1 | 10/2008 | Zhou et al. |
| 2016/0084757 A1 | 3/2016 | Miron |
| 2017/0315052 A1* | 11/2017 | Dasgupta ............... G01N 21/33 |

FOREIGN PATENT DOCUMENTS

| | | |
|---|---|---|
| GB | 2262338 A | 6/1993 |
| JP | 2001133403 A | 5/2001 |
| WO | 2008112955 A1 | 9/2008 |
| WO | 2013036378 A1 | 3/2013 |

OTHER PUBLICATIONS

Kaariainen et al., "Determining Biogenic Content of Biogas by Measuring Stable Isotopologues 12 CH4, 13CH4, and CH3D with a Mid-Infrared Direct Absorption Laser Spectrometer", Sensors, doi:10.3390/s18020496, 2018, 10 pages.
Written Opinion of The International Searching Authority, Application No. PCT/FI2020/050663, dated Dec. 18, 2020, 9 pages.

* cited by examiner

METHOD AND APPARATUS FOR ANALYZING GASEOUS SAMPLES

FIELD

Some embodiments relate to analyzing composition of a gaseous sample.

BACKGROUND

The composition of a gaseous sample may be analyzed by using direct absorption spectroscopy. For example, a respiratory air sample obtained from a subject may be analyzed by using direct absorption spectroscopy.

Figure 1A:
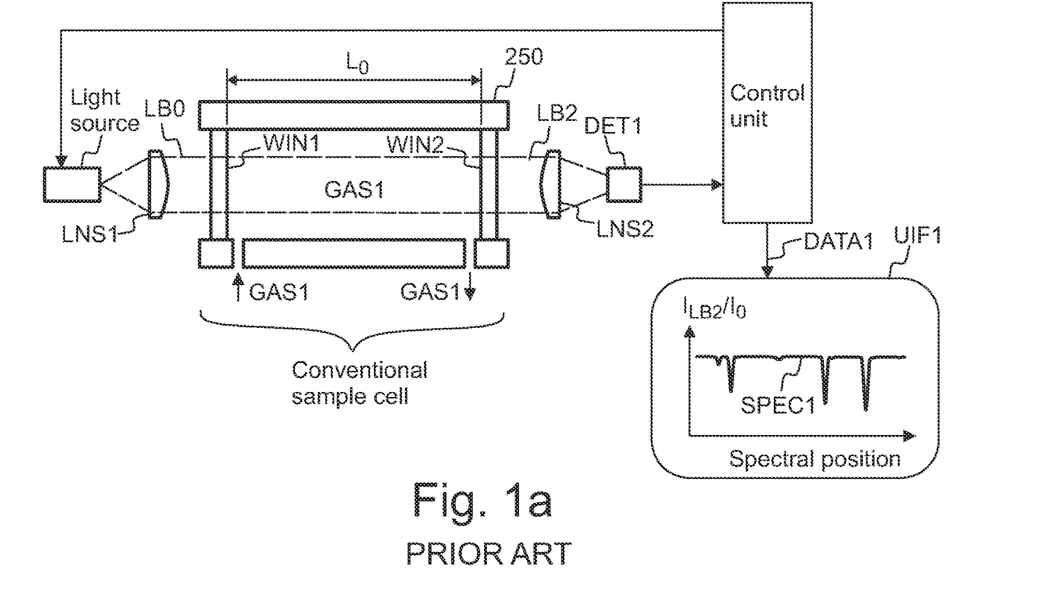
FIG. 1a shows, by way of example, a measuring apparatus, which comprises a sample cell according to prior art.

FIG. 1 shows a known measurement system for performing direct absorption spectroscopy. The known measurement system may comprise a sample cell for containing sample gas GAS1, a light source LS1 to provide illuminating light LB0, and a detector DET1 to detect light LB2 transmitted through the cell. The system may comprise collimating optics LNS1 to collimate the illuminating light LB0, and light gathering optics LNS2 to collect transmitted light LB2 to the detector DET1. The light source LS1 may tunable, i.e. the wavelength of the illuminating light LB0 may be adjustable. The illuminating light LB0 may have narrow bandwidth. The measurement system may measure a spectral transmittance function $I_{LB2}(\lambda)/I_0(\lambda)$ of a sample GAS1 by varying the wavelength $\lambda_{LB0}$ of the illuminating light LB0, and by measuring the intensity $I_{LB2}$ of the transmitted light LB2 as a function of the wavelength. An absorption spectrum SPEC1 of the sample GAS1 may be determined from the measured spectral transmittance $I_{LB2}(\lambda)/I_0(\lambda)$. The sample contained in the cell may attenuate the transmitted light at certain wavelengths, corresponding to the absorption peaks of the sample. Performing direct absorption spectroscopy may comprise measuring the spectral intensity of transmitted light at one or more spectral positions (wavelengths), and determining one or more properties of the sample by comparing the measured spectral intensity values with a reference value. Performing direct absorption spectroscopy may comprise measuring the spectral intensity of transmitted light at one or more spectral positions (wavelengths), and determining one or more properties of the sample by comparing the measured spectral intensity values with a reference spectrum. A reference spectrum of a reference gas may be obtained e.g. by filling the sample cell 200 with the reference gas, and by using the measuring device for measuring the spectral transmittance of the reference gas. For example, at a predetermined wavelength, the ratio $(I_{LB2}/I_0)$ of the spectral intensity $I_{LB2}$ of transmitted light LB2 to a reference value $I_0$ may depend on the concentration of a gaseous component of the sample. Consequently, the concentration of the gaseous component may be determined by measuring the spectral intensity $I_{LB2}$ of the transmitted light at one or more spectral positions, and by calculating the concentration of the gaseous component from the measured spectral intensity $I_{LB2}$ and from a reference value $I_0$. The reference value $I_0$ may be e.g. a maximum value of the spectral intensity of transmitted light LB2.

The sample cell typically comprises optical windows WIN1, WIN2 to confine the sample gas to the internal space of the cell, and to define the length of an absorption path. A part of the transmitted light may be reflected back and forth between the surfaces of the windows WIN1, WIN2. The windows of the sample cell may together operate as an interferometer, which may cause disturbing interference effects. In principle, any pair of optical surfaces may operate as an optical interferometer or as a weak optical interferometer.

Figure 1B:
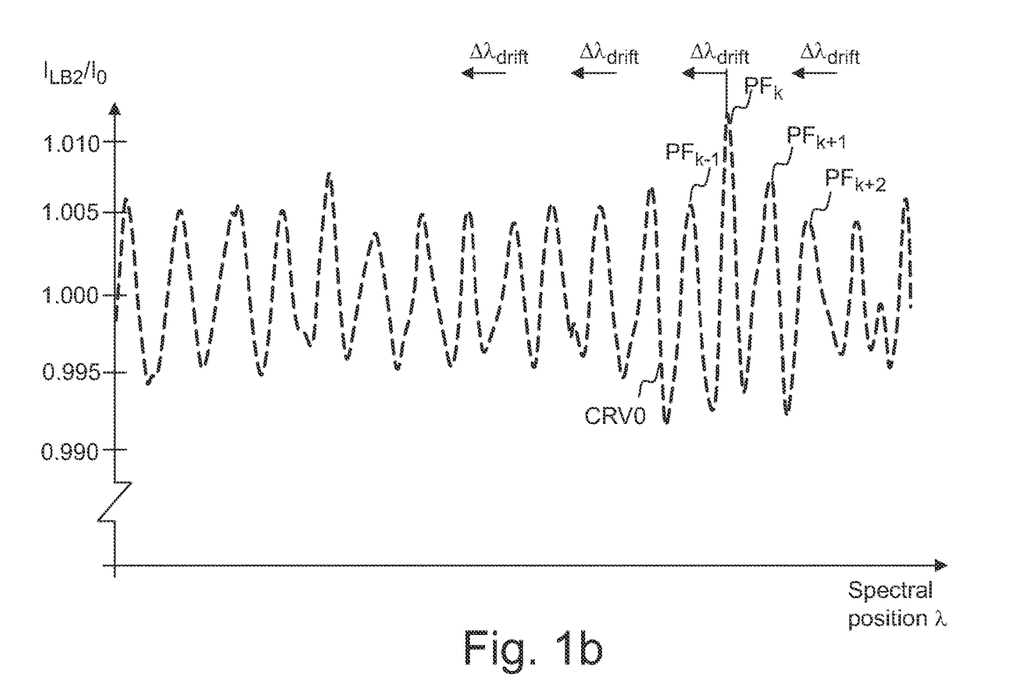
FIG. 1b shows, by way of example, measured spectral intensity of laser light transmitted through the sample cell of FIG. 1a, FIG. 2 shows, by way of example, in a cross-sectional side view, a measuring apparatus, which comprises a scrambling sample cell.

FIG. 1b shows, by way of example, a measured spectral intensity $I_{LB2}$ of light LB2, which has been transmitted through the conventional sample cell, in a situation where the cell is empty, and the illuminating beam is a collimated coherent laser beam. The measured intensity $I_{LB2}$ of FIG. 1a has been normalized by dividing with a reference value $I_0$.

A large part of the fluctuations of the measured signal $I_{LB2}$ may be caused by the interferometric fringes. A pair of optical interfaces of a conventional cell may cause disturbing interference effects. In particular, the interferometric effects of the windows of the conventional cell may make it difficult or impossible to detect weak absorption of a sample gas. Furthermore, detected spectral transmittance and results derived from the detected spectral transmittance may be prone to drift due to changes in interferometric response.

Interferometric effects of the cell may cause a plurality of spectral features to the spectral transmittance $I_{LB2}(\lambda)/I_0$ of the cell. The curve CRV0 shows, by way of example, the spectral transmittance $I_{LB2}(\lambda)/I_0(\lambda)$ of a conventional cell. The interferometric effects of the cell may cause a plurality of spectral features to the spectral transmittance $I_{LB2}(\lambda)/I_0$ of the cell also in a situation where the gas inside the cell does not absorb light. For example, the interferometric effects of the cell may cause a plurality of spectral interference peaks . . . , $PF_{k-1}$, $PF_k$, $PF_{k+1}$, $PF_{k+2}$, . . . to the spectral transmittance $I_{LB2}(\lambda)/I_0$ of the cell. The spectral positions of the spectral features $PF_{k-1}$, $PF_k$, $PF_{k+1}$, $PF_{k+2}$, . . . may drift e.g. due a change of operating temperature of the cell. The symbol $\Delta\lambda_{drift}$ may denote a spectral drift of the spectral features of the spectral transmittance $I_{LB2}(\lambda)/I_0$ of the cell.

When using the conventional sample cell, optical interference features $PF_{k-1}$, $PF_k$, $PF_{k+1}$, $PF_{k+2}$ typically exist due to a coherent nature of the laser radiation. In case of the conventional cell with coherent illumination, the periodic fluctuations of the detected spectral intensity $I_{LB2}$ may be too stable to be averaged out, whereas the periodic fluctuations of the detected spectral intensity $I_{LB2}$ are typically not stable enough to prevent the measurement results from drifting during a longer time period, e.g. during a time period of few minutes.

SUMMARY

Some variations may relate to a method for analyzing composition of a gaseous sample. Some variations may relate to an apparatus for analyzing composition of a gaseous sample. Some variations may relate to an apparatus for analyzing composition of a gaseous sample obtained from a processing system. Some variations may relate to a method for monitoring operation of a processing system. Some variations may relate to a method for analyzing composition of a respiratory air sample. Some variations may relate to an apparatus for analyzing composition of a respiratory air sample.

According to an aspect, there is provided a measuring apparatus (500) for measuring a spectrum (SPEC1) of a gaseous sample (GAS1), the apparatus (500) comprising:
  a tunable laser light source (LS1) to provide an illuminating light beam (LB0),
  a sample cell (200) for containing the gaseous sample (GAS1), the cell (200) comprising an inner surface (SRF1) to provide scrambled light (LB1) by reflecting light of the illuminating light beam (LB0) such that the scrambled light is transmitted through the gaseous sample (GAS1), a detector (DET1) to detect intensity ($I_{LB2}$) of transmitted scrambled light (LB2) guided through the sample cell (200), and a pressure control system (VAC1) to maintain an absolute pressure ($p_{GAS1}$) of the gaseous sample (GAS1) smaller than 50 kPa inside the sample cell (200) so as to reduce spectral widths of spectral features of the gaseous sample (GAS1), wherein the measuring apparatus (500) is arranged to measure one or more spectral transmittance values ($I_{LB2}(\lambda)/I_0(\lambda)$) of the sample (GAS1) by modulating the spectral position ($\lambda_{LB0}$) of the illuminating light (LB0), and by detecting the intensity ($I_{LB2}$) of the transmitted light (LB2) at two or more different spectral positions ($\lambda_0$, $\lambda_{P1}$) of the illuminating light (LB0), wherein the longitudinal dimension ($L_{SRF1}$) of the inner surface (SRF1) is in the range of 10 to 100 times a minimum diameter ($d_{SRF1}$) of the inner surface (SRF1), and wherein the divergence ($\theta_{LB0}$) of the illuminating light beam (LB0) in a transverse direction is greater than 30° so as to cause multiple consecutive reflections of the scrambled light (LB1) from the inner surface (SRF1).

According to an aspect, there is provided a method for measuring a spectrum (SPEC1) of a gaseous sample (GAS1), comprising:

providing an illuminating laser light beam (LB0), providing a sample cell (200) for containing the gaseous sample (GAS1), the cell (200) comprising an inner surface (SRF1), providing scrambled light (LB1) by using the inner surface (SRF1) to reflect light of the illuminating light beam (LB0) such that the scrambled light (LB1) is transmitted through the gaseous sample (GAS1), varying the spectral position ($\lambda_{LB0}$) of the illuminating light (LB0), detecting intensity ($I_{LB2}$) of transmitted scrambled light (LB2) guided through the sample cell (200) at two or more spectral positions ($\lambda_0$, $\lambda_{P1}$) of the illuminating light (LB0), and maintaining an absolute pressure ($p_{GAS1}$) of the gaseous sample (GAS1) smaller than 50 kPa inside the sample cell (200) so as to reduce spectral widths of spectral features of the gaseous sample (GAS1), wherein the longitudinal dimension ($L_{SRF1}$) of the inner surface (SRF1) is in the range of 10 to 100 times a minimum diameter ($d_{SRF1}$) of the inner surface (SRF1), and wherein the divergence ($\theta_{LB0}$) of the illuminating light beam (LB0) in a transverse direction is greater than 30°, so as to cause multiple consecutive reflections of the scrambled light (LB1) from the inner surface (SRF1).

Further aspects are defined in the claims.

When using the sample cell, the phase of the laser radiation is effectively scrambled inside the tightly confined, diffusive measurement tunnel, to significantly reduce or eliminate the disturbing effect of the optical interference features.

The internal pressure of the sample cell may be kept at a reduced value in order to facilitate measurement of the spectrum. The use of the reduced gas pressure may cause drifting of the interference features. The scrambling sample cell may significantly reduce or eliminate the disturbing effect of said drifting.

When using the phase-scrambling sample cell, it is not necessary to precisely align the scrambling sample cell with the optical axis of the illuminating laser beam.

Dust deposited on a window may increase reflection coefficient of the window. In case of a conventional cell, the increased reflection coefficient of the window may have a significant effect on the interference features caused by the windows of the cell. To a certain degree, the scrambling sample cell may be tolerant to dust, which may be deposited on the windows. The scrambling sample cell may reduce or eliminate interference effects caused by dust deposited on a window of the cell.

A diverging laser beam may be directly transmitted into the scrambling tunnel of the cell. The tunnel may have a diffusive uneven inner surface. Multiple reflections of the laser light inside the tunnel may scramble the phase of the coherent light, effectively suppressing the optical interference.

When using the scrambling sample cell, it is not necessary to use long averaging or integrating time periods to reduce signal noise caused by the interference effects Consequently, the spectral data may be measured at an increased rate, when compared with a situation where spectral data is measured by using a conventional cell. The phase-scrambling cell may substantially reduce or eliminate amplitudes of interference features. The phase-scrambling cell may substantially reduce or eliminate amplitudes of interference fringes. The reduced fringe amplitudes in the phase-scrambling cell may allow increasing the length of a time period between consecutive calibrations. The phase-scrambling cell may even completely remove a need for periodic calibration. The scrambling sample cell may be used as a single-pass absorption cell. The scrambling sample cell may be used e.g. for measuring carbon monoxide CO and/or carbon dioxide by direct absorption spectroscopy.

A measuring apparatus may comprise the scrambling cell in order to suppress the interferometric fringe effect. The measuring apparatus may be arranged to analyze composition of a gaseous sample by direct absorption spectroscopy. The measuring apparatus may be arranged to analyze e.g. the composition of a respiratory air sample obtained from a subject.

In an embodiment, the measuring apparatus may be arranged to analyze the composition of the sample obtained from an industrial processing system. The processing system may comprise e.g. an apparatus for producing combustible gas by fermentation of biological material. The operation of the processing system may be controlled, analyzed and/or optimized based on the analysis.

In an embodiment, the measuring apparatus may be arranged to analyze the composition of the sample e.g. in order to determine one or more physical and/or metabolic parameters of the body of the subject. The measured information may be used e.g. to monitor a state of the body of the subject. The measured information may comprise e.g. information about the concentration of an anesthetic agent in the respiratory air sample. The measured information may be used e.g. for controlling an anesthetic system.

BRIEF DESCRIPTION OF THE DRAWINGS

In the following examples, several variations will be described in more detail with reference to the appended drawings, in which.

DETAILED DESCRIPTION

Figure 2:
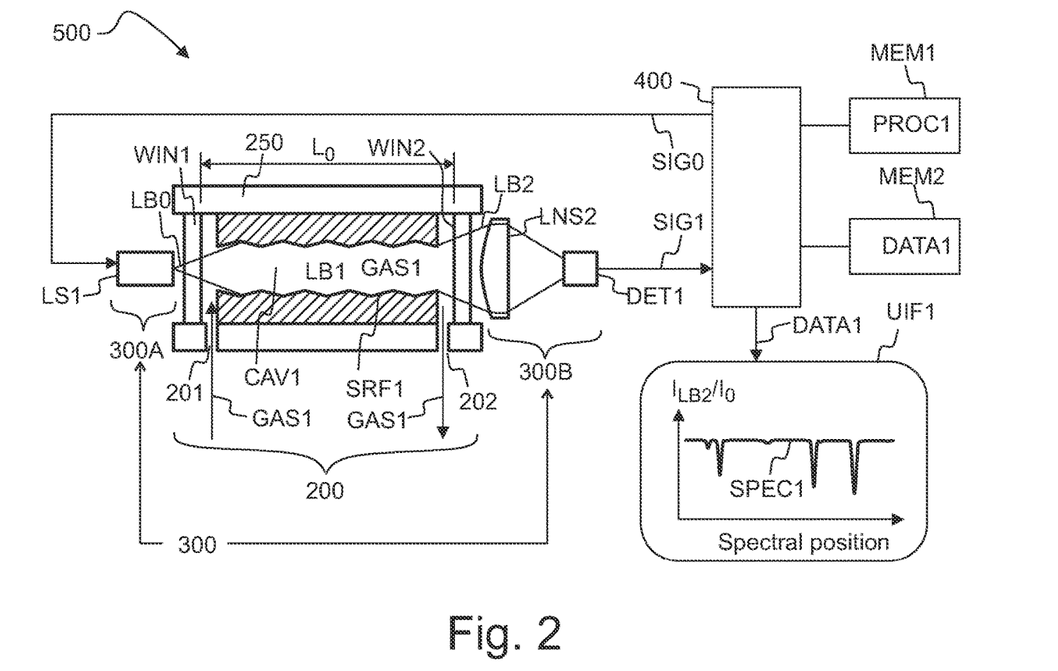

Referring to FIG. 2, the measuring apparatus 500 may comprise a sample cell 200 for containing a sample gas GAS1, a light source LS1 to provide illuminating light LB0, and a detector DET1 to detect intensity of transmitted light LB2, which has been transmitted through the sample cell 200. The illuminating light LB0 is coupled into the sample cell 200. The illuminating light LB0 may also be called e.g. as input light LB0.

The sample cell 200 may comprise a housing 250, a first window WIN1 and a second window WIN2 to confine the sample gas GAS1 to the internal space of the cell 200. Illuminating light LB0 may be coupled into the cell 200 through the first window WIN1. The transmitted light LB2 may be coupled out of the cell 200 through the second window WIN2. The cell 200 may comprise a first window WIN1 for coupling light into the cell 200, and a second window WIN2 for coupling light out of the cell 200. The distance between the windows WIN1, WIN2 may define an inner longitudinal dimension $L_0$ of the cell 200.

The cell 200 may comprise an input 201 for guiding sample gas GAS1 into the cell 200 and an output 202 for guiding sample gas GAS1 out of the cell 200. The cell 200 may comprise one or more openings 201, 202 for changing the contents of the cell 200. A first sample may be replaced with a second sample by using the one or more openings 201, 202. The sample gas GAS1 may be moved into the cell and out of the cell e.g. by using a sample pump. The sample gas GAS1 inside the cell may also be substantially continuously changed during a measuring time period, so as to measure temporal changes of the composition and/or state of the sample GAS1.

The cell 200 may comprise a scrambling tunnel CAV1 to form scrambled light LB1 by reflecting light of the illuminating beam LB0. The tunnel CAV1 may comprise an uneven surface SRF1 to form scrambled light LB1 by reflecting light of the illuminating beam LB0. The internal space of the tunnel CAV1 may be defined by the surface SRF1. The tunnel CAV1 may consist of the surface SRF1 and the internal space. The scrambled light LB1 may be guided via the tunnel CAV1 through the cell 200. Transmitted scrambled light LB2 may be coupled out of the cell 200 through the second window WIN2. Multiple reflections of the light from the uneven surface SRF1 may effectively smooth out spectral interference effects of the windows WIN1, WIN2.

In case of the uneven surface SRF1, the effective length of optical absorption path of the cell 200 may be greater than the distance $L_0$ between the windows WIN1, WIN2. If needed, the effective length of optical absorption path of the cell 200 may be determined e.g. by an experimental test and/or by simulation. The effective length of optical absorption path of the cell 200 may be experimentally determined e.g. by filling the cell 200 with a reference gas, which has a known concentration of an absorbing gaseous component, by measuring the spectral transmittance at one or more relevant wavelengths, by calculating transmittance values from known data, and by determining the length of optical absorption path by fitting calculated transmittance values to the measured transmittance values.

In an embodiment the ratio of a concentration of a first gaseous component to the concentration of a second gaseous component may also be determined from measured spectral transmittance values without a need to know the actual effective length of the optical absorption path. It may be assumed that the effective length of the optical absorption path is substantially the same for both gaseous components.

The sample GAS1 contained in the scrambling cell 200 may provide the transmitted beam LB2 by absorbing light of the scrambled light beam LB1 according to the absorption spectrum of said sample GAS1. In particular, the sample GAS1 may attenuate the spectral intensity at wavelengths corresponding to spectral peaks of the absorption spectrum of the sample GAS1.

The apparatus 500 may comprise an optical assembly 300, which comprises an illuminating unit 300A and a detector unit 300B. The illuminating unit 300A may comprise the light source LS1. The detector unit 300B may comprise the detector DET1.

The illuminating light LB0 may have a narrow spectral bandwidth, so as to allow measuring spectral absorbance by using spectrally selective illumination. The bandwidth of the light LB0 may be e.g. smaller than 0.02 nm. The light source LS1 may be e.g. a laser light source. The illuminating light LB0 may be e.g. coherent laser light. The wavelength $\lambda_{LB0}$ of the illuminating light LB0 may be changed in order to measure spectral transmittance values of the filled cell 200 at several spectral positions. The absorbance values may be subsequently determined from the transmittance values. The wavelength XLB0 of the illuminating light LB0 may be changed in order to measure spectral absorbance values of the filled cell 200 at several spectral positions. The wavelength of the light emitted by the light source LS1 may be tunable. The light source (LS1) may be a tunable laser such that the wavelength ($\lambda_{LB0}$) of the illuminating light beam (LB0) is adjustable. For example, the light source LS1 may be a laser diode, wherein the wavelength of the light LB0 may be changed e.g. by changing an electric current of the laser diode LS1. The light source LS1 may be a laser diode, wherein the wavelength of the light LB0 may be changed e.g. by changing an electric current of the laser diode LS1 and/or by changing operating temperature of the laser diode LS1.

The light source LS1 may be arranged to provide the illuminating light LB0 as a diverging beam. The diverging beam of illuminating light LB0 may effectively interact with the inner surface SRF1 of the sample cell 200, so as to ensure sufficient degree of phase scrambling. The light source LS1 may be e.g. a laser light emitter. In an embodiment, it is not necessary to use collimating optics or focusing optics to reduce the divergence of illuminating light emitted from a laser light emitter. In an embodiment, the apparatus 500 does not need to comprise collimating optics or focusing optics between a laser light emitter and the sample cell 200. In an embodiment, the apparatus 500 may be implemented without collimating and/or focusing optics located between a light emitter and the sample cell 200.

The illuminating light beam LB0 may be coupled from a laser emitter LS1 into the scrambling tunnel CAV1 without using collimating and/or focusing optics located between the laser emitter LS1 and the tunnel CAV1.

The focal length of optics between the laser emitter LS1 and the tunnel CAV1 may be e.g. greater than 0.02 m, in order to maintain large divergence of the illuminating beam LB0. The refractive power of the optics is equal to inverse of the focal length. The illuminating light beam LB0 may be coupled from a laser emitter LS1 into the scrambling tunnel CAV1 such that the refractive power of optics between the laser emitter LS1 and the tunnel CAV1 is e.g. smaller than 50 dioptre.

The light source LS1 may comprise e.g. an interband cascade laser (ICL) or a quantum cascade laser (QCL).

The light source LS1 may be a tunable laser light source such that wavelength $\lambda_{LB0}$ of at least one spectral component of the illuminating light beam LB0 is adjustable.

The apparatus 500 may comprise a control unit 400 to change the spectral position $\lambda$ of the illuminating light LB0, and to record the measured intensity $I_{LB2}$ of the transmitted light LB2 as a function of the spectral position $\lambda$. The apparatus 500 may be configured to provide spectral data DATA1, SPEC1 by associating measured spectral intensity values $I_{LB2}$ with the corresponding spectral positions ($\lambda$).

The control unit 400 may provide a control signal SIG0 for changing the wavelength of the illuminating light LB0. The control signal SIG0 may be communicated to the light source LS1. The light source LS1 may be arranged to modulate the wavelength of the illuminating light LB0. The apparatus 500 may be arranged to provide a signal SIG0 indicative of the wavelength of the illuminating light LB0.

The detector DET1 may be arranged to provide a signal SIG1 indicative of the detected spectral intensity of the transmitted light LB2. The signal SIG1 may be e.g. an electric signal or a digital optical signal. The detector DET1 may comprise e.g. one or more photodiodes or one or more photomultiplier tubes to convert intensity of the light LB2 into a signal value of the signal SIG1.

The detector may be arranged to detect light LB2 e.g. in the middle infrared range.

The detector DET1 may comprise e.g. Mercury-Cadmium-Telluride (MCT), indium arsenide antimonide (InAsSb), or germanium (Ge).

The apparatus 500 may be configured to provide spectral data DATA1 by associating each measured intensity value of the transmitted light LB2 with the corresponding spectral position of the illuminating light LB0. The apparatus 500 may be configured to provide measured spectral data DATA1, which comprises spectral intensity values of the gas sample. The apparatus 500 may comprise a memory MEM2 for storing the measured spectral data DATA1. The apparatus 500 may comprise a memory MEM1 for storing computer program code PROC1. The computer program code PROC1 may be configured to, when executed by the control unit 400, to modulate the wavelength of the illuminating light LB0 and/or to form spectral data DATA1 by associating measured intensity values with corresponding spectral positions.

The apparatus 500 may comprise computer program code PROC1 stored in computer readable memory MEM1. The program code PROC1, when executed by the control unit 400, may cause the apparatus 500 to measure the spectral data DATA1. The control unit 400 may comprise one or more data processors. The measured data DATA1 may be stored e.g. in a memory MEM2. The apparatus 500 may comprise a user interface UIF1 for receiving user input from a user and/or for providing the measured data DATA1 to a user. The apparatus 500 may comprise a user interface UIF1 to provide one or more measurement results to a user. The user interface UIF1 may comprise e.g. a display for graphically and/or numerically displaying measured and/or determined values. The apparatus 500 may be arranged to display curves, which show temporal evolution of the measured values. The user interface UIF1 may comprise e.g. a display and/or a keyboard. The user interface UIF1 may comprise e.g. a touch screen. The user interface may display e.g. a measured spectrum SPEC1 of the sample GAS1. The user input and/or the data DATA1 may be transmitted e.g. via a cable, via a wireless communication network and/or via the Internet.

Figure 3:
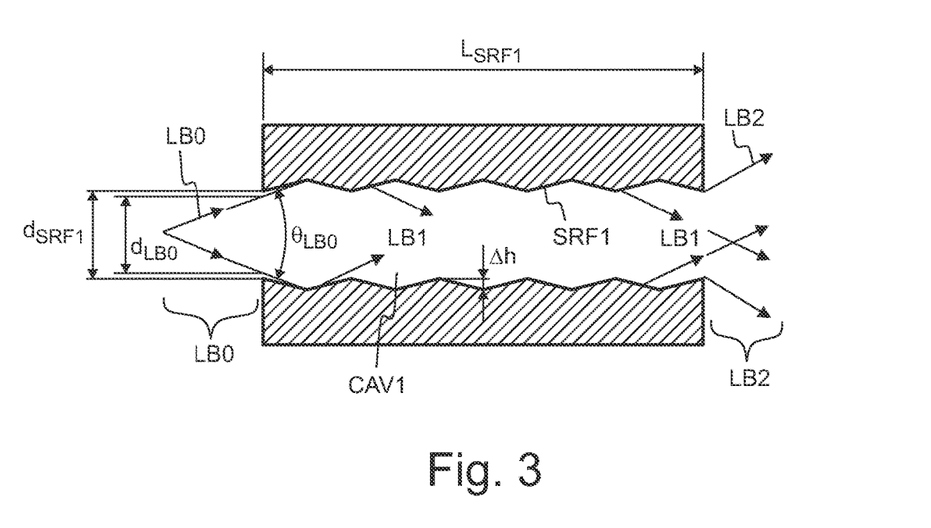
FIG. 3 shows, by way of example, in a cross-sectional side view, propagation of light in the scrambling sample cell.

Referring to FIG. 3, the diverging illuminating beam LB0 may be coupled from a laser light source LS1 through the first window WIN1 into the scrambling tunnel CAV1. The tunnel CAV1 may be defined by the uneven reflective surface SRF1.

The longitudinal dimension $L_0$ of the scrambling sample cell may be e.g. smaller than 0.5 m. The longitudinal dimension $L_{SRF1}$ of the inner surface SRF1 of the cell 200 may be smaller than 0.5 m, respectively.

The cross-section of the tunnel CAV1 may be e.g. substantially circular or substantially elliptical, when viewed in the direction of propagation of the input light beam LB0. The cross-section of the tunnel CAV1 may be e.g. substantially circular or substantially elliptical, when viewed in the longitudinal direction of the tunnel CAV1.

The diameter $d_{SRF1}$ of the tunnel may be e.g. in the range of 0.5 mm to 6 mm. The diameter $d_{SRF1}$ of the tunnel may be e.g. substantially equal to 3 mm. The tunnel CAV1 may effectively scramble the phase of the illuminating light LB0.

The dimensions of the tunnel CAV1 may be selected to provide several consecutive reflections from the surface SRF1, so as to effectively scramble the phase of the light LB1 and LB2. The scrambling tunnel may have a longitudinal dimension $LSRF_1$. The ratio of the length $L_{SRF1}$ to the diameter $d_{SRF1}$ of the tunnel may be e.g. greater than or equal to 10. The ratio of the longitudinal dimension $L_{SRF1}$ to the diameter $d_{SRF1}$ of the tunnel may be e.g. in the range of 10 to 100, e.g. in order to provide sufficient degree of scrambling in a compact volume.

The roughness of the inner surface SRF1 of the tunnel CAV1 may be selected e.g. such that the specular reflectance of the inner surface SRF1 is smaller than 50%, advantageously smaller than 10%.

The roughness of the inner surface SRF1 of the tunnel CAV1 may be selected e.g. such that the specular reflectance of the inner surface SRF1 is smaller than 50%, advantageously smaller than 10% at the wavelength $\lambda_{LB0}$ of the illuminating light LB0.

The symbol Δh may denote an average height of protrusions of the surface SRF1.

The arithmetic mean roughness Ra of the inner surface SRF1 may be e.g. in the range of 0.25 to 2 times the wavelength $\lambda_{LB0}$ of the illuminating light LB0.

The wavelength $\lambda_{LB0}$ of the light source LS1 may be e.g. in the range of 4.3 μm to 4.4 μm.

The arithmetic mean roughness Ra of the inner surface SRF1 may be e.g. in the range of 0.5 μm to 8 μm.

The distances between (microscopic) roughness features of the inner surface SRF1 may exhibit random or pseudo-random variation so as to minimize or eliminate interference effects. The roughness features may comprise e.g. protrusions and depressions whose height or depth is e.g. in the range of 0.1 μm to 40 μm. The surface SRF1 may be processed e.g. by abrasive blasting, by etching and/or by depositing a coating material so as to provide randomly positioned roughness features, whose height or depth is in the range of 0.1 μm to 40 μm. The surface SRF1 may comprise randomly positioned protrusions and/or depressions such that the arithmetic mean roughness Ra of the inner surface SRF1 is e.g. in the range of 0.5 μm to 8 μm.

The inner surface SRF1 may be produced such that the specular reflectance of the inner surface SRF1 is e.g. smaller than 50%, so as to ensure sufficient scrambling in the cell. The specular reflectance of the inner surface SRF1 may be e.g. smaller than 10%, so as to ensure high degree of scrambling in the cell.

The inner surface SRF1 may be produced such the total reflectance of the inner surface SRF1 is greater than e.g. 80% at the wavelength $\lambda_{LB0}$ of the illuminating light beam LB0, so as to ensure sufficient intensity of the transmitted light LB2. The total reflectance may be measured e.g. at an angle of incidence of 80%.

$d_{LB0}$ denotes a transverse dimension of the illuminating beam LB0 at the input end of the tunnel CAV1. The transverse dimension $d_{LB0}$ may be e.g. in the range of 30% to 95% of the diameter $d_{SRF1}$ of the tunnel CAV1. The transverse dimension $d_{LB0}$ may be smaller than the diameter $d_{SRF1}$ e.g. in order to reduce or eliminate optical feedback to the light source LS1.

The light source LS1 may provide illuminating light LB0 as an illuminating light beam. The illuminating beam LB0 may have a divergence $\theta_{LB0}$. The divergence $\theta_{LB0}$ of the illuminating beam LB0 in a transverse direction may be e.g. greater than 20°.

The light source LS1 may be e.g. a laser emitter. A laser beam LB0 emitted from a laser emitter may have a fast axis direction and a slow axis direction. The fast axis direction is transverse with respect to the longitudinal direction of propagation of the laser beam LB0. The slow axis direction may be perpendicular to the fast axis direction and perpendicular to the longitudinal direction of the laser beam LB0.

The divergence $\theta_{LB0}$ of the illuminating beam LB0 in the transverse fast axis direction may be e.g. greater than 20°.

The illuminating beam LB0 may be coupled into the cell 200 as a diverging beam. Coupling the illuminating beam LB0 into the cell 200 as the diverging beam may further suppress the interferometric effects, by increasing the number of the reflections from the uneven phase-scrambling surface SRF1.

The longitudinal dimension $L_{SRF1}$ of the inner surface SRF1 may be e.g. in the range of 10 to 100 times a minimum diameter $d_{SFR1}$ of the inner surface SRF1, and the divergence $\theta_{LB0}$ of the illuminating light beam LB0 in a transverse direction may be e.g. greater than 30° so as to cause multiple consecutive reflections of the scrambled light LB1 from the inner surface SRF1, before the scrambled light LB1 is coupled out of the cell 200 as the transmitted light LB2.

The number of the multiple consecutive reflections of the scrambled light LB1 from the inner surface SRF1 may be in a suitable range e.g. in order to ensure sufficient degree of scrambling, wherein also ensuring a sufficient intensity of the transmitted light LB2.

When using the diverging beam LB0, the first optics LNS1 (FIG. 1a) may be simplified or eliminated. The diverging beam may be provided without using the first optics LNS1. Eliminating the first optics LNS1 may reduce interference effects cause by the first optics LNS1.

The optical assembly 300 may optionally comprise light gathering optics LNS2 to collect light LB2 to the detector DET1. The light gathering optics LNS2 may comprise e.g. one or more lenses to focus light LB2 to the detector DET1. A lens of the optics LNS2 may be optionally arranged to operate also as the optical window WIN2 of the cell 200, in order to reduce the number of optical surfaces.

In an embodiment, the optical assembly 300 may also be implemented without the light gathering optics LNS2.

In an embodiment, a transparent output element of the light source LS1 may be arranged to operate as the first window WIN1.

In an embodiment, a transparent input element of the detector DET1 may be arranged to operate as the second window WIN2.

A transparent output element of the light source LS1 operating as a window WIN1 and/or a transparent input element of the detector DET1 operating as a window WIN2 may define the longitudinal dimension $L_0$ of the cell 200.

In an embodiment, the first window WIN1 and/or the second window WIN2 may have an inclined orientation to further reduce disturbing reflections.

In an embodiment, the first window WIN1 and/or the second window WIN2 may have a wedge shape to further reduce disturbing reflections.

Figure 4:
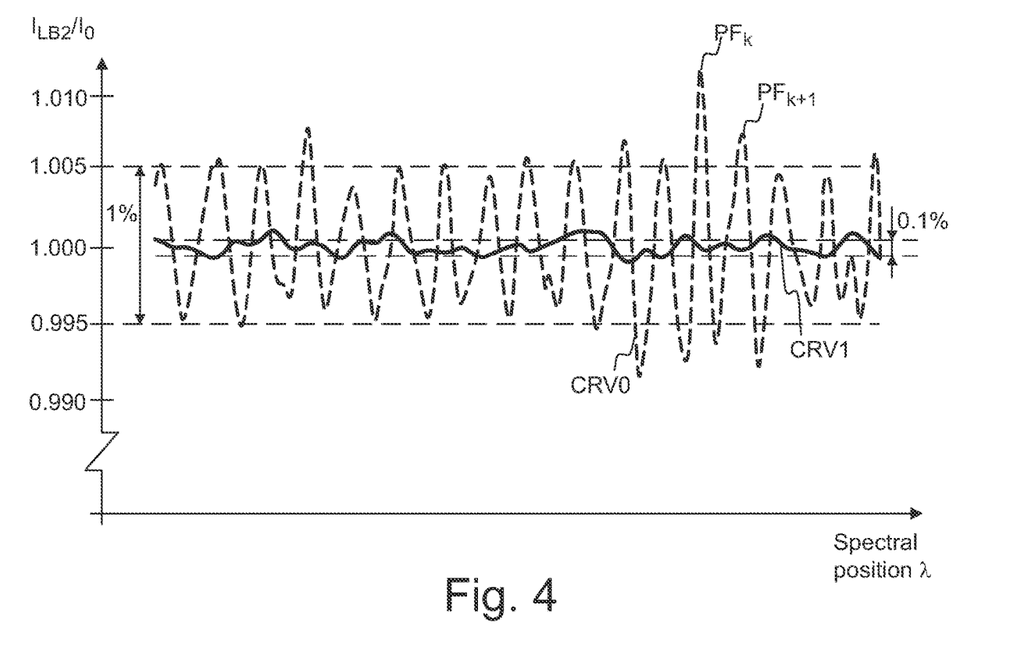
FIG. 4 shows, by way of example, measured spectral intensity of laser light transmitted through the scrambling sample cell, and measured spectral intensity of laser light transmitted through the conventional sample cell of FIG. 1a, FIG. 5 shows, by way of example, spectral intensity of the transmitted light as a function of spectral position, in a situation where the scrambling sample cell contains an absorbing sample.

Referring to FIG. 4, the scrambling tunnel CAV1 may effectively suppress the interferometric fringe effects caused by the windows WIN1, WIN2. The solid curve CRV1 shows, by way of example, the spectral transmittance $I_{LB2}(\lambda)/I_0(\lambda)$ of the scrambling sample cell 200. The spectral transmittance $I_{LB2}(\lambda)/I_0(\lambda)$ may be determined from the measured spectral intensity of light LB2 transmitted through the scrambling sample cell 200. The dashed curve CRV0 shows, by way of example, the spectral transmittance $I_{LB2}(\lambda)/I_0(\lambda)$ of the conventional sample cell (see FIGS. 1a and 1b).

In case of a conventional cell, the relative height of the (disturbing) spectral features $PF_k$, $PF_{k+1}$, ... caused by the interference effects may be e.g. in the order of 1%. In case of the scrambling cell, the relative height of (disturbing) spectral features may be substantially smaller, e.g. in the order of 0.1%. Thus, the scrambling cell may allow detecting a smaller relative deviation $(I_0(\lambda_{P1})-I_{LB2}(\lambda_{P1}))/(I_0(\lambda_{P1})$ caused by an absorbing spectral line of a gaseous sample GAS1 at a spectral position $\lambda_{P1}$. The deviation $(I_0(\lambda_{P1})-I_{LB2}(\lambda_{P1}))$ may represent a "signal", and the reference intensity $(I_0(\lambda_{P1})$ may represent a "background".

The scrambling cell may allow measurements at a lower signal-to-background ratio. A smallest detectable signal-to-background ratio (e.g. in the order of 0.1%) of the scrambling sample cell 200 may be substantially smaller than a smallest detectable signal-to-background ratio (e.g. in the order of 1%) of the conventional cell. The scrambling sample cell 200 may allow detecting a smaller concentration of an absorbing gas. Using the scrambling sample cell 200 may allow measuring the concentration of an absorbing gas with better accuracy. Using the scrambling sample cell 200 may allow measuring spectral data at a higher speed, when compared with the conventional cell.

Figure 5:
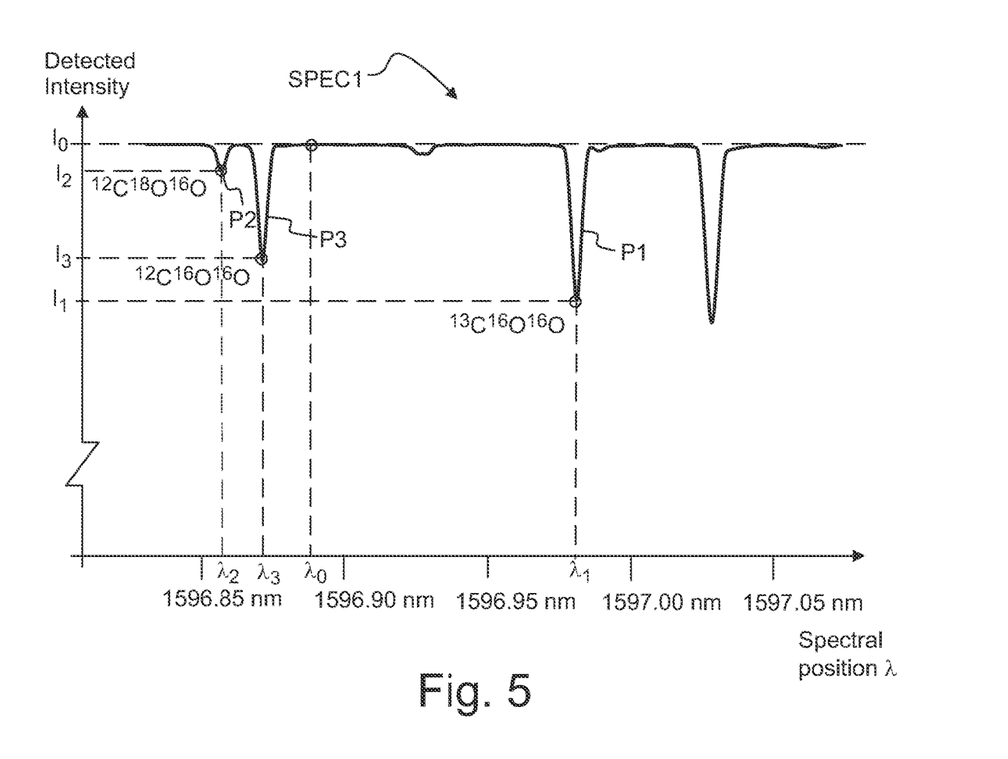

FIG. 5 shows, by way of example, an absorption spectrum of a gas sample GAS1 which contains the carbon isotope $^{13}C$ and the oxygen isotope $^{18}O$ bound in carbon dioxide $CO_2$, in addition to the normal carbon dioxide isotope compound $^{12}C^{16}O^{16}O$. An isotope compound molecule may also be called e.g. as an isotopologue. Isotopologues are molecules that differ only in their isotopic composition.

A spectral intensity value $I_1(\lambda_1)$ associated with $^{13}C^{16}O^{16}O$ may be measured by setting the wavelength of the narrowband illuminating light LB0 to a first spectral position $\lambda_1$. A spectral intensity value $I_2(\lambda_2)$ associated with $^{12}C^{16}O^{16}O$ may be measured by setting the wavelength of the light LB0 to a second spectral position $\lambda_2$. A spectral intensity value $I_3(\lambda_3)$ associated with $^{12}C^{16}O^{16}O$ may be measured by setting the wavelength of the light LB0 to a third spectral position $\lambda_3$. A reference intensity value $I_0(\lambda_0)$ may be measured by setting the wavelength of the narrowband illuminating light LB0 to a fourth spectral position $\lambda_0$. In an embodiment, the reference intensity $I_0(\lambda)$ may also be a (non-constant) function of the wavelength $\lambda$.

The first spectral position $\lambda_1$ may substantially coincide with a first spectral peak P1 of the isotope compound $^{13}C^{16}O^{16}O$. The second spectral position $\lambda_2$ may substantially coincide with a second spectral peak P2 of the isotope compound $^{12}C^{18}O^{16}O$. The third spectral position $\lambda_3$ may substantially coincide with a third spectral peak P3 of the isotope compound $^{12}C^{16}O^{16}O$. The full spectrum of the $CO_2$ comprises a high number of peaks associated with the rotational-vibrational energy states of the different isotopes. The positions $\lambda_1$, $\lambda_2$, $\lambda_3$ may be selected from the spectral positions of the peaks of the $CO_2$ spectrum such that the peaks at the positions $\lambda_1$, $\lambda_2$, $\lambda_3$ do not significantly overlap with each other. The fourth spectral position $\lambda_0$ may be selected such that it does not overlap with any spectral peak of the sample GAS1. The positions $\lambda_0$, $\lambda_1$, $\lambda_2$, $\lambda_3$ may also coincide with different spectral peaks than what is shown in FIG. 3.

The method may comprise guiding a gas sample GAS1 into the scrambling cell 200, and measuring e.g. the concentration of $^{13}C^{16}O^{16}O$ of the sample GAS1 by measuring the spectral intensity of the transmitted light LB2.

Figure 6A:
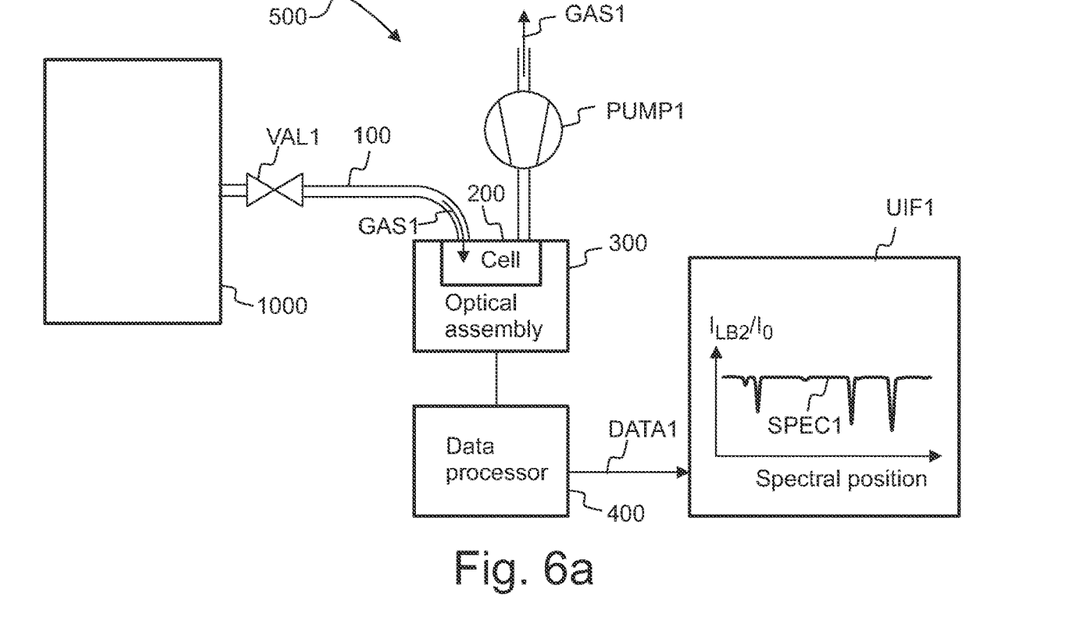
FIG. 6a shows, by way of example, a measuring apparatus arranged to measure the concentration of one or more molecular substances of a gaseous sample obtained from a processing system.

Referring to FIG. 6a, the measuring apparatus 500 may be arranged to analyze the composition of a gaseous sample GAS1. The sample gas GAS1 may be obtained e.g. from a processing system 1000. The processing system 100 may be e.g. an industrial processing system. The system 1000 may be arranged to carry out e.g. a combustion process, a chemical process and/or a biochemical process.

The measuring apparatus 500 may be arranged to measure a spectrum SPEC1 of a sample GAS1 obtained from the processing system 1000. The measuring apparatus 500 may be arranged to analyze a sample GAS1 obtained from the processing system 1000. The measuring apparatus 500 may be arranged to analyze the sample GAS1 e.g. by comparing the measured spectrum SPEC1 with reference data. The measuring apparatus 500 may be arranged to analyze the sample GAS1 e.g. by comparing the measured spectrum SPEC1 with a reference spectrum. The operation of the system 1000 may be controlled and/or optimized based on the analysis. The system 1000 may be arranged to control operation of said system 1000 based on the measured spectral data SPEC1, DATA1.

The system 1000 may be arranged to carry out e.g. a biological fermentation process. The system 1000 may be e.g. a fermentation system arranged to produce combustible gas from biological material. The measuring apparatus 500 may be arranged to measure e.g. the relative concentration of one or more of the following substances: carbon dioxide $CO_2$, water vapor $H_2O$, methane $CH_4$, ethylene $C_2H_4$, isotope $^{18}O$ bound in $CO_2$, isotope $^{13}C$ bound in $CO_2$, isotope $^{17}O$ bound in $CO_2$, isotope $^{18}O$ bound in water vapor $H_2O$, methane $CH_4$, ethylene $C_2H_4$, isotope $^{13}O$ bound in ethylene $C_2H_4$.

The sample gas GAS1 may be guided to the cell 200 e.g. via a sampling line 100. The apparatus 500 may optionally comprise one or more valves VAL1 for controlling flow rate of the sample gas GAS1 into the cell 200. The valve VAL1 may also be arranged to regulate an internal pressure of the sample cell 200. The apparatus 500 may optionally comprise e.g. a pump PUMP1 for causing a flow of the sample gas GAS1 into the cell 200. The optical measuring assembly 300 may be arranged to measure absorption spectrum of the sample GAS1 contained in the cell 200. The optical measuring assembly 300 may be arranged to provide spectral data DATA1 by measuring absorption spectrum (SPEC1) of the sample GAS1 contained in the cell 200.

Figure 6B:
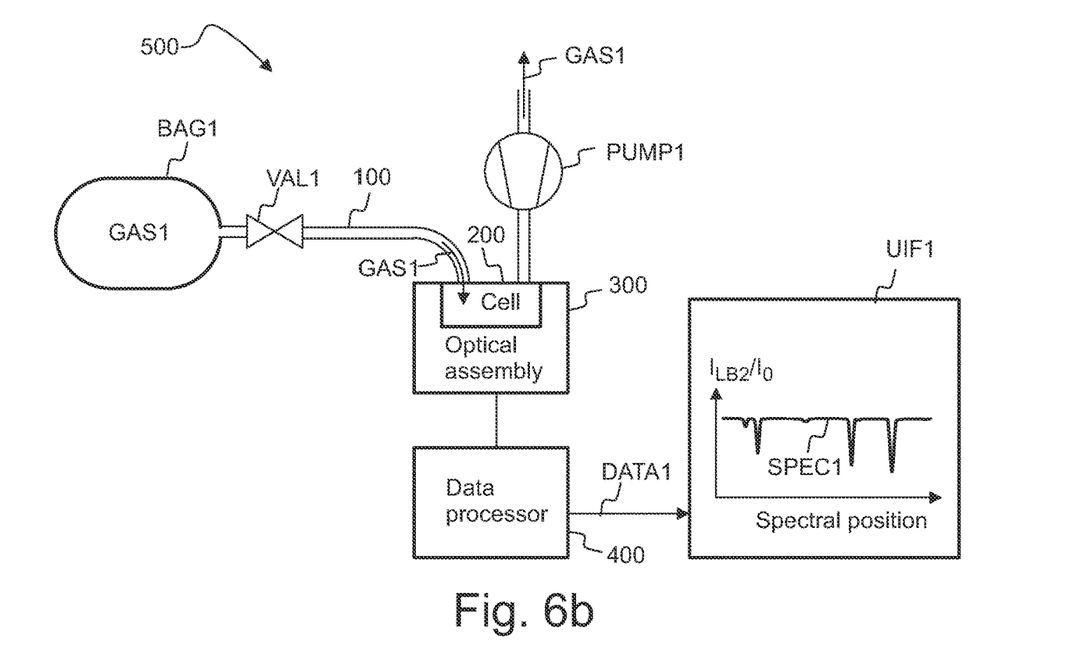
FIG. 6b shows, by way of example, a measuring apparatus arranged to measure the concentration of one or more molecular substances of a gaseous sample.

Referring to FIG. 6b, the apparatus 500 may be arranged to analyze the composition of a gaseous sample GAS1. The sample gas GAS1 may be guided to the cell 200 e.g. from a container BAG1. The sample gas GAS1 may be stored and/or transported in a container BAG1. The container BAG1 may be transportable and/or portable. The container BAG1 may be e.g. a bag, a vial, a test tube, or a gas cylinder. The container BAG1 may comprise e.g. flexible plastic foil coated with metal foil. The sample gas GAS1 may be guided from the container BAG1 to the cell 200 via a sampling line 100. The container BAG1 may comprise one or more valves for closing and opening the container. The apparatus 500 may optionally comprise e.g. a pump PUMP1 for causing a flow of the sample gas GAS1 into the cell 200. Gas pressure inside the container BAG1 may also be so high that a gas flow from the container to the cell 200 may be caused simply by opening the valve VAL1.

The optical measuring assembly 300 may be arranged to measure absorption spectrum of the sample GAS1 contained in the cell 200. The optical measuring assembly 300 may be arranged to provide spectral data DATA1 by measuring absorption spectrum (SPEC1) of the sample GAS1 contained in the cell 200.

Figure 6C:
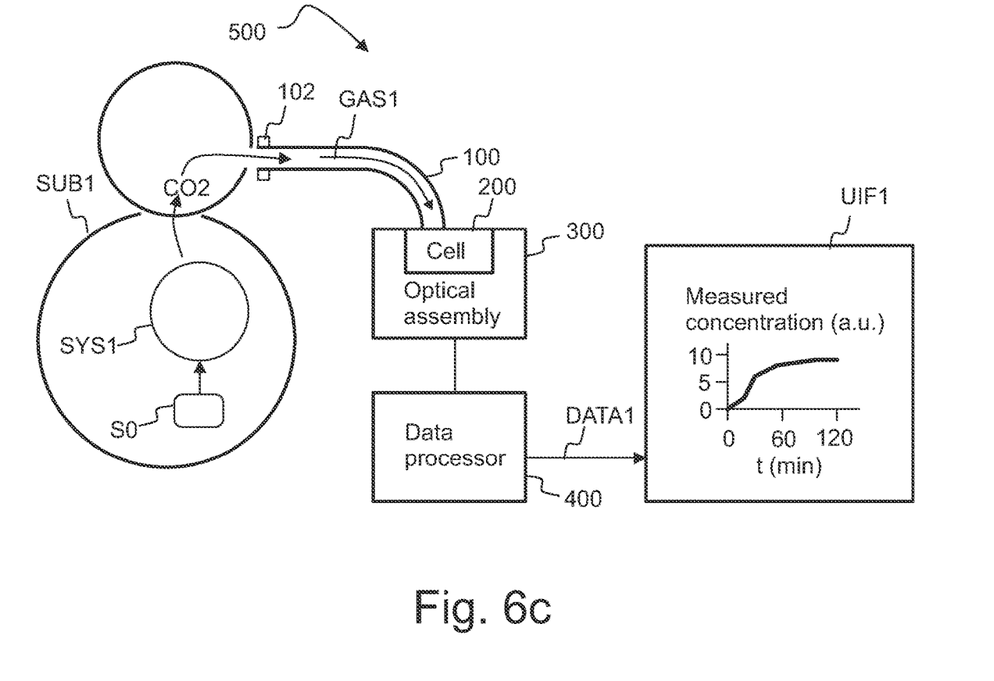
FIG. 6c shows, by way of example, a measuring apparatus arranged to measure the concentration of one or more molecular substances of a gaseous sample.

Referring to FIG. 6c, the apparatus 500 may be arranged to analyze e.g. the composition of a respiratory air sample GAS1 obtained from a subject SUB1 The apparatus 500 may comprise a sampling line 100 for guiding an exhaled air sample GAS1 to the cell 200. The sampling line 100 may comprise e.g. a mask portion 102 to temporarily seal the sampling line 100 to the mouth and/or nose of the subject SUB1.

The optical measuring assembly 300 may be arranged to measure absorption spectrum of the sample GAS1 contained in the cell 200. The optical measuring assembly 300 may be arranged to provide spectral data DATA1 by measuring absorption spectrum of the sample GAS1 contained in the cell 200.

The apparatus 500 may be arranged to monitor e.g. the concentration of an anesthetic agent in the respiratory air sample GAS1 obtained from the subject.

The apparatus 500 may be arranged to monitor e.g. the ratio of a concentration of a first gaseous component to the concentration of a second gaseous component.

The apparatus 500 may be arranged to measure e.g. the concentration of $^{13}C$ bound in carbon dioxide of a respiratory air sample GAS1 obtained from a subject SUB1. The apparatus 500 may be arranged to measure e.g. the concentration of the isotope compound $^{13}C^{16}O^{16}O$ to the concentration of the isotope compound $^{12}C^{16}O^{16}O$ in the sample GAS1.

The respiratory air sample GAS1 may be obtained e.g. after administering a substance S0, which comprises $^{13}C$. The measured concentration of $^{13}C$ may be used e.g. for measuring a metabolic rate of the subject. The metabolic rate of the first subject SUB1 may be measured by a method, which comprises measuring the concentration of carbon isotope $^{13}C$ in the respiratory air of the first subject SUB1, after an amount of the substance S0 has been administered to the first subject SUB1.

A part of the isotope $^{13}C$ may be converted into carbon dioxide $CO_2$ via one or more metabolic pathways in the body of the subject, after administering the test substance. The method may comprise sampling and analyzing respiratory air, which has been exhaled by the subject. The subject SUB1 has a metabolic system SYS1, which may provide one or more metabolic pathways for the substance S0 in the body of the subject SUB1. The subject SUB1 may be e.g. a human being, or an animal. The metabolic system SYS1 may comprise e.g. one or more internal organs of the subject SUB1.

Several gases may have absorbing transitions in the middle infrared range (MID-IR), i.e. at wavelengths, which are in the spectral range of 2.5 µm to 10 µm. The light source LS1 may be arranged to emit light at one or more wavelengths, which are in range of 2.5 µm to 10 µm, and the detector DET1 may be arranged to detect the light LB2 transmitted through the sample cell 200.

Figure 7:
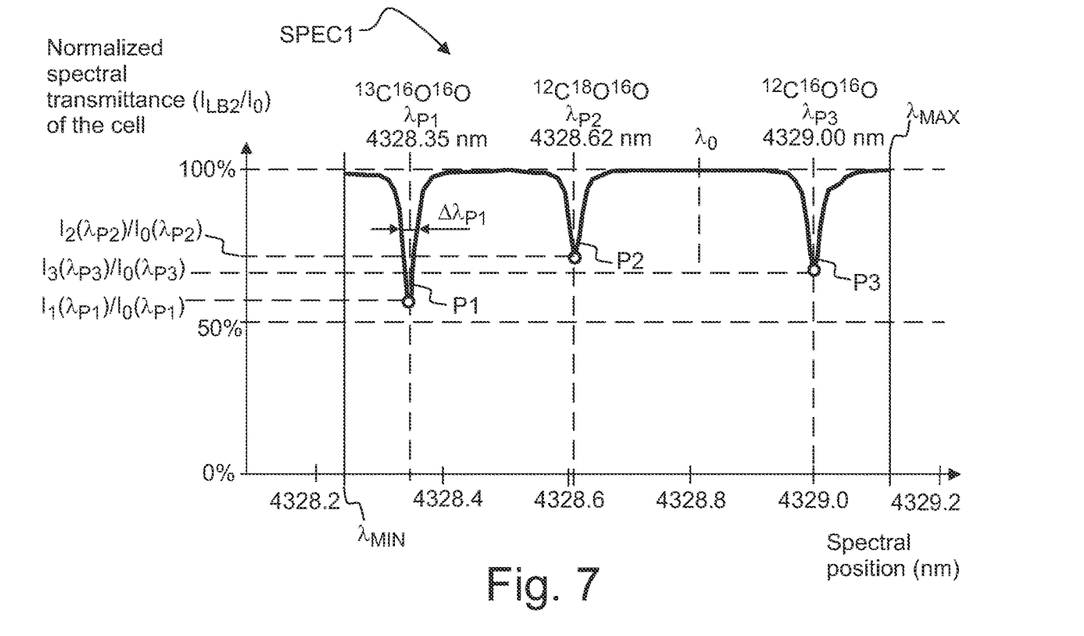
FIG. 7 shows, by way of example, an absorption spectrum of a sample gas.

Referring to FIG. 7, the apparatus 500 may be arranged to measure the concentration of one or more gaseous components of the sample gas GAS1 by measuring the intensity $I_{LB2}$ of the transmitted light LB2 at one or more wavelengths ($\lambda_0, \lambda_{P1}, \lambda_{P2}, \lambda_{P3}$), which are in the a spectral range from a first wavelength limit $\lambda_{MIN}$ to a second wavelength limit $\lambda_{MAX}$. The method may comprise modulating the wavelength $\lambda_{LB0}$ of the illuminating light e.g. in a spectral modulating range of $\lambda_{MIN}$ to $\lambda_{MAX}$.

The absorption lines of the sample gas GAS1 may be detected e.g. as local minima P1, P2, P3 of the spectral transmittance $I_{LB2}(\lambda)/I_0(\lambda)$. The absorption lines may be detected e.g. as the (inverse) absorption peaks P1, P2, P3 of the transmittance spectrum. The spectral transmittance $I_{LB2}(\lambda)/I_0(\lambda)$ may attain local minimum e.g. at spectral positions $\lambda_{P1}, \lambda_{P2}, \lambda_{P3}$. Each peak P may have a spectral width $\Delta\lambda_P$. For example, the absorption line represented by the inverse peak P1 may have a spectral width $\Delta\lambda_{P1}$. The spectral width $\Delta\lambda_{P1}$ may be e.g. a full-width-at-half maximum width. The spectral width $\Delta\lambda_{P1}$ may mean e.g. the spectral width at the spectral positions where the transmitted intensity $I_{LB2}$ is equal to $(I_0(\lambda_{P1})-(I_0(\lambda_{P1})-I_{LB2}(\lambda_{P1}))/2)$.

The spectral width $\Delta\lambda_{P1}$ of a gaseous substance may depend on the pressure of the sample gas GAS1. The spectral width $\Delta\lambda_{P1}$ may be reduced by reducing the pressure of the sample gas GAS1. Reducing the pressure may improve effective spectral resolution and/or detection limit of the measuring apparatus, for measuring one or more substances in a gaseous sample. Reducing the pressure may facilitate measuring the concentration of a gaseous substance.

Reducing the pressure may facilitate measuring the ratio of concentrations of gaseous substances.

For example, the apparatus 500 may be arranged to measure the concentration of $^{13}C$ bound in carbon dioxide of a breathing air sample GAS1, by measuring the intensity $I_{LB2}$ of the transmitted light LB2 at one or more wavelengths ($\lambda_0, \lambda_{P1}, \lambda_{P2}, \lambda_{P3}$), which are e.g. in the spectral range of 4328.2 nm to 4329.2 nm. The wavelength $\lambda_{LB0}$ of the light source LS1 may be e.g. in the range of 4.3 µm to 4.4 µm.

The method may comprise guiding a gas sample GAS1 into the scrambling cell 200, and measuring the concentration of $^{13}C^{16}O^{16}O$ of the sample GAS1 by measuring the spectral intensity of the transmitted light LB2.

The method may comprise guiding a gas sample GAS1 into the scrambling cell 200, and measuring the concentration of $^{12}C^{18}O^{16}O$ of the sample GAS1 by measuring the spectral intensity of the transmitted light LB2.

The method may comprise guiding a gas sample GAS1 into the scrambling cell 200, and measuring the concentration of $^{12}C^{16}O^{16}O$ of the sample GAS1 by measuring the spectral intensity of the transmitted light LB2.

The method may comprise guiding a gas sample GAS1 into the scrambling cell 200, and measuring a ratio of the concentration of carbon isotope $^{13}C$ bound in carbon dioxide to the concentration of carbon isotope $^{12}C$ bound in carbon dioxide by detecting spectral transmittance of carbon dioxide at three or more spectral positions ($\lambda_0, \lambda_1, \lambda_2$).

Figure 8A:
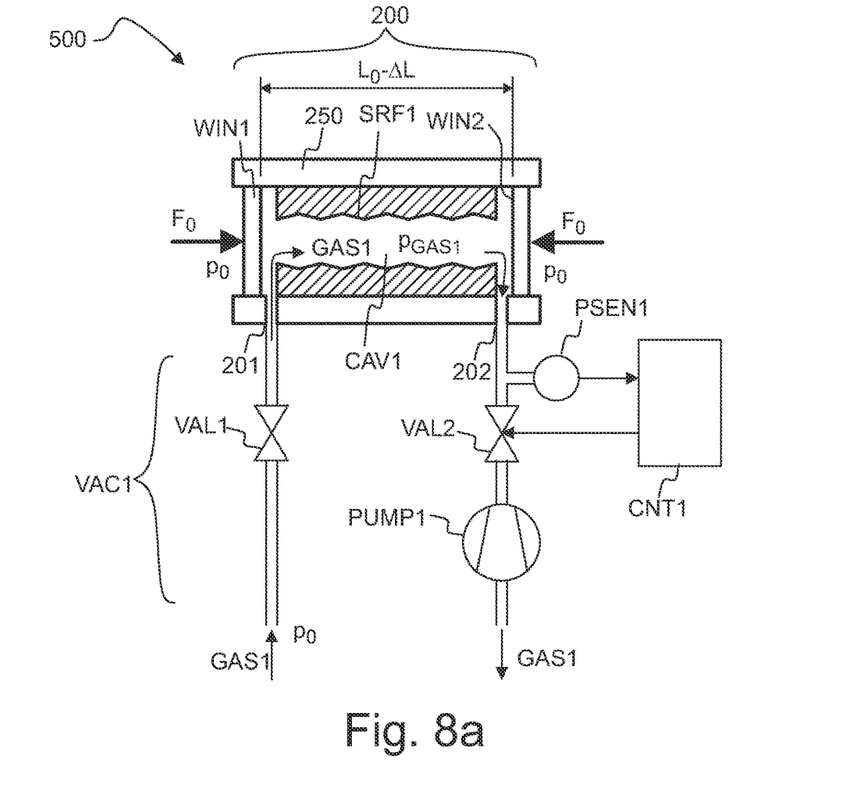
FIG. 8a shows, by way of example, a pressure control system for reducing and controlling internal pressure of the sample cell.

Referring to FIG. 8a, the measuring apparatus 500 may further comprise a pressure control system VAC1 to control the internal pressure of the sample cell 200. The system VAC1 may be arranged to keep the internal pressure $p_{GAS1}$ of the sample cell 200 at a predetermined value. The pressure control system VAC1 may reduce the internal pressure $p_{GAS1}$.

The system VAC1 may be arranged to keep the absolute pressure $p_{GAS1}$ of the sample gas GAS1 inside the sample cell 200 e.g. lower than 50 kPa (i.e. lower than 500 mbar). The system VAC1 may be arranged to keep the absolute pressure pcAsi e.g. in the range of 1 kPa to 50 kPa (10 mbar to 500 mbar). The system VAC1 may be arranged to keep the absolute pressure $p_{GAS1}$ e.g. substantially equal to 7.5 kPa (75 mbar). Keeping the pressure $p_{GAS1}$ at a low value may reduce the spectral width (e.g. $\Delta\lambda_{P1}$) of spectral features of the spectrum SPEC1, by reducing an effect of spectral pressure broadening. Reducing the effect of the spectral pressure broadening may provide e.g. a lower signal noise and/or may provide a lower detection limit.

The pressure control system VAC1 may comprise e.g. a first orifice VAL1, a second orifice VAL2, a pump PUMP1, a pressure sensor PSEN1, and a pressure control unit CNT1. The first orifice VAL1 may be e.g. a fixed orifice or an adjustable valve. The second orifice VAL2 may be e.g. a fixed orifice or an adjustable valve. The pump PUMP1 may be arranged to draw gas out of the cell 200, so as to reduce the internal pressure of the cell 200. The pump PUMP1 may draw sample gas GAS1 into the cell 200 through the first orifice VAL1. The pressure difference po-pcAsi over the first orifice VAL1 may depend on the flow rate of the sample gas GAS1 through said first orifice VAL1. $p_0$ may denote the ambient pressure. The ambient pressure may be e.g. substantially equal to 100 kPa. The pump PUMP1 and the first orifice VAL1 may be arranged to provide a pressure difference po-pcAsi. The partial vacuum system VAC1 may comprise a pressure sensor PSEN1 to monitor the internal pressure pcAsi. The pressure control unit CNT1 may be arranged to keep the internal pressure pcAsi at a predetermined value e.g. by controlling operation of one or more of the valves VAL1, VAL2 and/or by controlling operation of the pump PUMP1. The pump PUMP1 may be e.g. a piston pump, a diaphragm pump or an ejector.

Using the scrambling cell 200 under the reduced pressure pcAsi may reduce disturbing interference effects. The interference effects may include e.g. mechanical deformation of the cell 200. The pressure difference (po-pcAsi) may deform and/or may displace the windows WIN1, WIN2 so as to cause drifting of the spectral positions of the interference peaks (see e.g. the drifting $\Delta\lambda_{drift}$ of the peak $PF_k$ in FIG. 1b). The pressure difference may cause forces $F_0$, which may deform the cell 200. The pressure forces $F_0$ may e.g. cause a change $\Delta L$ of the longitudinal dimension $L_0$ of the cell 200.

The pressure difference (po-pcAsi) may also cause a change of the refractive index of the sample gas GAS1 inside the cell 200. The change of the refractive index may also cause drifting of the spectral positions of the interference peaks, by causing a corresponding change of the effective length of the optical path inside the cell 200. Using the scrambling cell 200 may reduce the disturbing interference effects caused by the low gas pressure inside the cell.

The optional pressure reduction system VAC1 may provide improved spectral resolution, detection limit and/or accuracy of the apparatus 500.

However, the apparatus 500 may also be implemented without the pressure reduction system VAC1, e.g. in order to reduce manufacturing costs.

The measuring apparatus 500 may comprise:
a tunable laser light source LS1 to provide an illuminating light beam LB0,
a sample cell 200 for containing the gaseous sample GAS1, the cell 200 comprising an inner surface SRF1 to provide scrambled light LB1 by reflecting light of the illuminating light beam LB0 such that the scrambled light is transmitted through the gaseous sample GAS1, and
a detector DET1 to detect intensity $I_{LB2}$ of transmitted scrambled light LB2 guided through the sample cell 200, wherein the measuring apparatus 500 is arranged to measure one or more spectral transmittance values ($I_{LB2}(\lambda)/I_0(\lambda)$) of the sample GAS1 by modulating the spectral position $\lambda_{LB0}$ of the illuminating light LB0, and by detecting the intensity $I_{LB2}$ of the transmitted light LB2 at two or more different spectral positions ($\lambda_0, \lambda_{P1}$) of the illuminating light LB0, wherein a longitudinal dimension $L_{SRF1}$ of the inner surface SRF1 is in the range of 10 to 100 times a minimum diameter $d_{SRF1}$ of the inner surface SRF1, and wherein the divergence $\theta_{LB0}$ of the illuminating light beam LB0 in a transverse direction is greater than 20° so as to cause multiple consecutive reflections of the scrambled light LB1 from the inner surface SRF1.

Figure 8B:
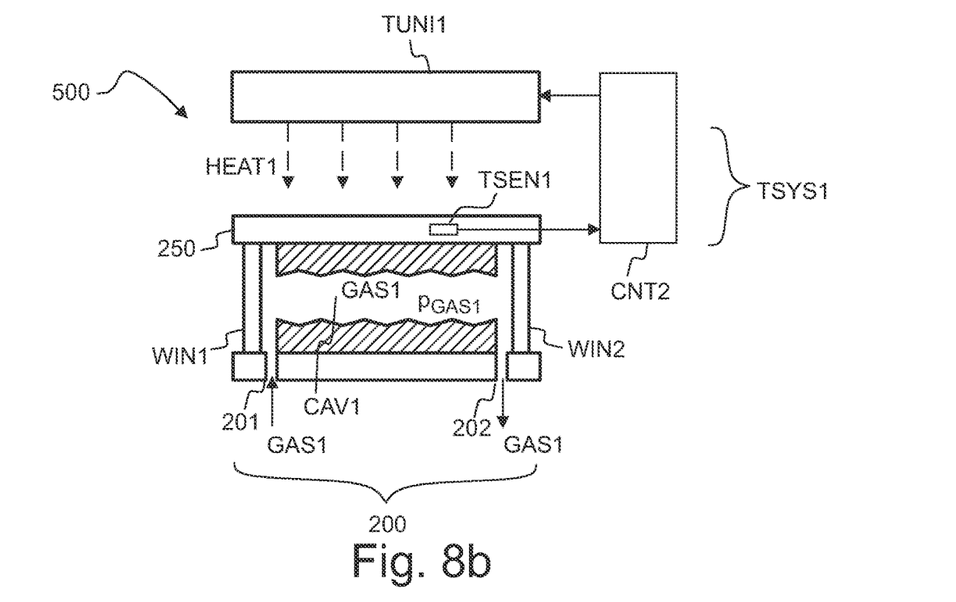
FIG. 8b shows, by way of example, a temperature control system for stabilizing temperature of the sample cell.

Referring to FIG. 8b, the apparatus 500 may further comprise a temperature control system TSYS1 to stabilize the operating temperature of the sample cell 200. The temperature control system TSYS1 may comprise e.g. a heater unit TUNI1 to heat the sample cell 200, a temperature sensor TSEN1 to measure the operating temperature of the sample cell 200, and a temperature control unit CNT2 to control the heating based on the measured operating temperature. The temperature control system TSYS1 may comprise a heating unit TUNI1 to increase the operating temperature of the cell 200. The heating unit TUNI1 may be e.g. a resistive electric heater.

The cell 200 may also be cooled instead or in addition to heating. The temperature control system TSYS1 may be arranged to heat and/or cool the cell 200. The temperature control system TSYS1 may comprise a cooling unit TUNI1 to decrease the operating temperature of the cell 200. The cooling unit TUNI1 may comprise e.g. a Peltier cooler.

The apparatus 500 optionally comprise a temperature control system to stabilize and/or to modulate operating temperature of the light source LS1. For example, the apparatus 500 may be arranged to adjust an operating temperature of a laser light source LS1 in order to modulate the wavelength of the illuminating light LB0.

The apparatus 500 optionally comprise a temperature control system to stabilize operating temperature of the detector DET1.

Figure 9A:
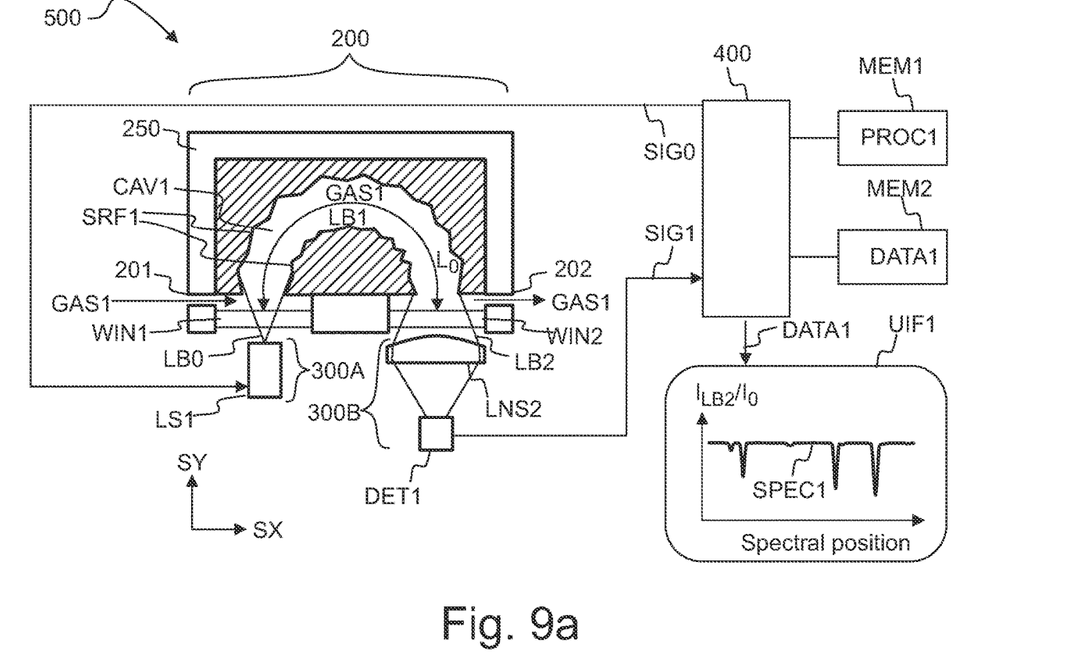
FIG. 9a shows, by way of example, in a cross-sectional side view, a nonlinear sample cell.
Figure 9B:
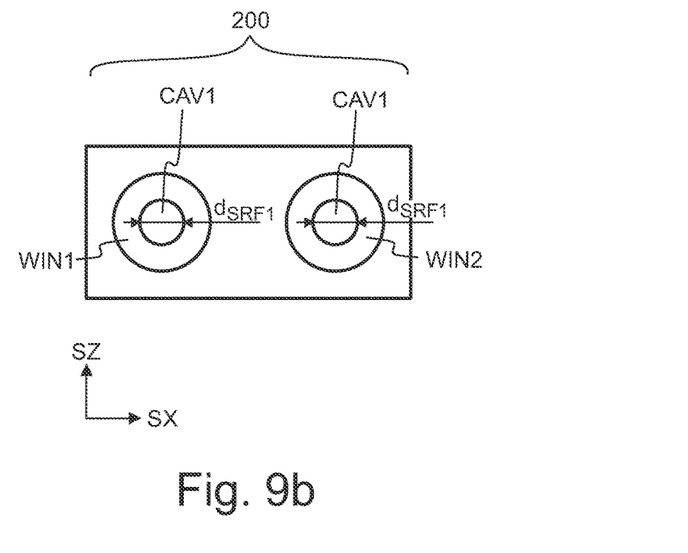
FIG. 9b shows, in an end view, the sample cell of FIG. 9a, and FIG. 10 shows, by way of example, measuring temporal evolution of a concentration of an absorbing substance.

Referring to FIGS. 9a and 9b, the tunnel CAV1 may also be curved. A nonlinear tunnel CAV1 may comprise one or more curved portions. For example, a centerline curve of the tunnel CAV1 from the input end to the output end may have the shape of the (Latin alphabet) character "U". The longitudinal dimension L0 of the cell 200 may be measured from the inner surface of the input window WIN1 to the inner surface of the output window WIN2 along the nonlinear centerline curve of the tunnel CAV1.

The initial direction of propagation the illuminating light beam (LB0) may be e.g. substantially opposite to the direction of propagation the transmitted light LB2, which is coupled out of the sample cell 200. This arrangement may enable e.g. mounting the light source LS1 and the detector DET1 on the same support element, so as to provide a stable and compact structure. The tunnel CAV1 may have one or more curved portions e.g. in order to allow mounting the light source LS1 and the detector DET1 on the same support element.

A nonlinear tunnel CAV1 may be produced e.g. by mechanical machining and by processing the inner surface. A nonlinear tunnel CAV1 may be produced e.g. by bending a section of a metal tube, and by processing the inner surface. A linear tunnel CAV1 as shown e.g. in FIG. 3 may be produced e.g. by drilling a piece of metal, and by processing the inner surface. The inner surface may be processed e.g. grinding, by abrasive blasting, by etching and/or by depositing a coating. The inner surface SRF1 of the sample cell 200 may comprise e.g. aluminum, silver, gold, platinum, or rhodium. The inner surface may be optionally coated with a protective coating.

Figure 10:
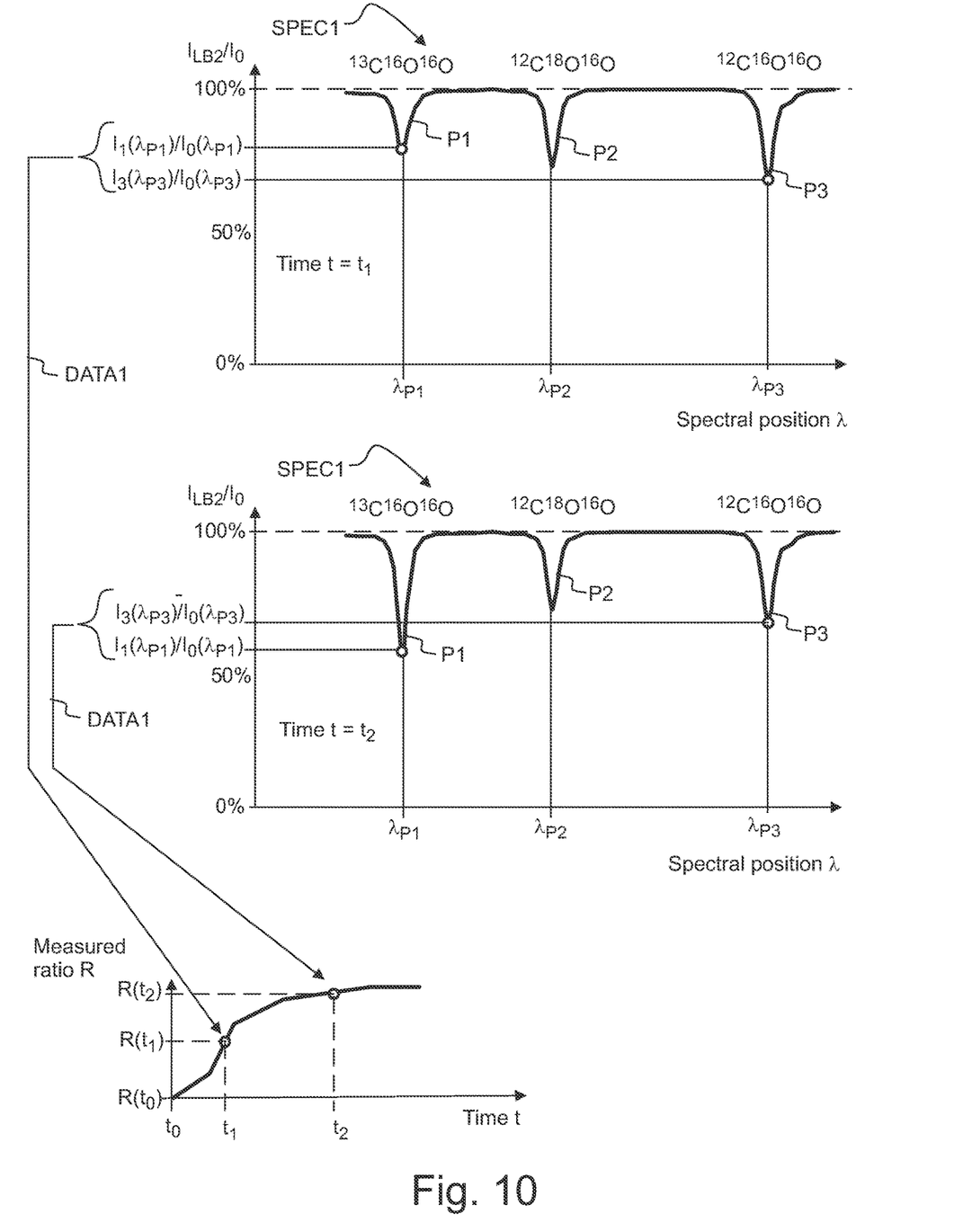

Referring to FIG. 10, the apparatus 500 may be arranged to measure temporal evolution of concentration of a substance. The apparatus 500 may be arranged to measure concentration as a function of time (t). The apparatus 500 may be arranged to measure temporal evolution of a ratio R of a concentration of a first substance to a concentration of a second substance. The apparatus 500 may be arranged to measure the ratio as a function of time (t). The first substance may be e.g. $^{13}C^{16}O^{16}O$. The second substance may be e.g. $^{12}C^{16}O^{16}O$.

The ratio R may have an initial value $R(t_0)$ at a time $t_0$. The ratio R may have a first value $R(t_1)$ at a time $t_1$. The ratio R may have a second value $R(t_2)$ at a time $t_2$. The initial value $R(t_0)$ may be measured e.g. immediately after administering an amount of the substance S0 to a subject SUB1. The first value $R(t_1)$ and the second value $R(t_2)$ may be measured after administering the amount of the substance S0, at the times $t_1$ and $t_2$.

The initial value $R(t_0)$ may represent a reference state of the system 1000 or a reference state of a subject SUB1. The initial value $R(t_0)$ may also be called e.g. as a reference value of the measured concentration ratio, as a baseline value of the measured concentration ratio, or as a background value of the measured concentration ratio. The initial value $R(t_0)$ may also be measured e.g. before administering an amount of the substance S0 to a subject SUB1.

The system may measure a spectral transmittance function $I_{LB2}(\lambda)/I_0(\lambda)$ of a sample GAS1 by varying the wavelength of the illuminating light LB0, and by measuring the intensity of the transmitted light LB2 as a function of the wavelength. An absorption spectrum SPEC1 of the sample GAS1 may be subsequently determined from the measured spectral transmittance function $I_{LB2}(\lambda)/I_0(X)$.

At a predetermined wavelength $\lambda$, the ratio $(I_{LB2}/L_0)$ of the spectral intensity $I_{LB2}$ of transmitted light LB2 to a reference value $I_0$ may depend on the concentration of a gaseous component of the sample, on the interaction length ($L_0$), on the temperature $T_{GAS1}$ of the sample gas GAS1 and/or on the pressure $p_{GAS1}$ of the sample gas GAS1. Consequently, the concentration of the gaseous component may be determined by measuring the spectral intensity $I_{LB2}$ of the transmitted light at one or more spectral positions, and by calculating the concentration of the gaseous component from the measured spectral intensity $I_{LB2}$ and from a reference value $I_0$.

The concentration of the gaseous component may also be determined by fitting a line profile to the measured function $I_{LB2}(\lambda)/I_0(\lambda)$ in the vicinity of an absorption peak of the gaseous component.

The concentration of the gaseous component may be determined from an absorption line area of the function $I_{LB2}(\lambda)/I_0(\lambda)$.

A first gaseous component may form a first absorption line by absorbing light at a first wavelength. A second gaseous component may form a second absorption line by absorbing light at a second different wavelength. The method may comprise comparing an area of a first absorption line to an area of a second absorption line. The method may comprise measuring a ratio of concentration of the first gaseous component to the concentration of the second gaseous component. The method may comprise determining a ratio of the concentration of the first component to the concentration of the second component based on the ratio of the area of the first absorption line to the area of the second absorption line.

For measuring a ratio of concentrations of isotopes, the second component may be e.g. the most abundant isotopologue of a molecule, and the first component may be e.g. a less abundant isotopologue of the same molecule.

The reference value $I_0$ may be e.g. a maximum value of the spectral intensity of transmitted light LB2. The reference value $I_0$ and/or the reference function $I_0(\lambda)$ may be determined e.g. by measuring an absorption spectrum of a (non-absorbing) reference gas sample, which does not comprise absorbing molecules in the spectral range of the measurement. The reference gas sample may be e.g. synthetic air, which does not comprise carbon dioxide. The reference gas sample may be formed e.g. by forming a mixture of pure gases or by removing carbon dioxide from an ambient air sample.

The "area" of the absorption line refers to an integral of the wavelength dependent absorption signal $(I_{LB2}(\lambda)/I_0(\lambda))$ over a spectral range, which includes the central wavelength (e.g. $\lambda_{P1}$) of the spectral line (e.g. P1).

The spectral width of an absorption line profile may depend e.g. mainly on temperature-dependent Doppler broadening and on pressure-induced collisional broadening.

The method may comprise fitting a theoretical line profile to the measured data. The method may comprise e.g. determining a peak absorbance, temperature broadening, and/or pressure broadening by fitting a mathematical model, e.g. a Voigt profile, to the measured absorption data.

The method may further comprise determining a spectral scale of the measured data based on measured spectral positions of one or more spectral lines. Theoretical spectral positions of the spectral lines may be determined e.g. by using the high-resolution transmission molecular absorption database (HITRAN). The HITRAN database has been developed and maintained by the Atomic and Molecular Physics Division, Harvard-Smithsonian Center for Astrophysics.

Performing direct absorption spectroscopy may comprise measuring the spectral intensity of transmitted light at one or more spectral positions (wavelengths), and determining one or more properties of the sample by comparing the measured spectral intensity values with a reference value. Performing direct absorption spectroscopy may comprise measuring the spectral intensity of transmitted light at one or more spectral positions (wavelengths), and determining one or more properties of the sample by comparing the measured spectral intensity values with a reference spectrum. A reference spectrum of a reference gas may also be obtained e.g. by filling the sample cell 200 with the (non-absorbing) reference gas, and by using the measuring apparatus 500 for measuring the spectral transmittance of the reference gas.

The reference intensity $I_0(\lambda)$ may also be a (non-constant) function of the wavelength $\lambda$. For example, the wavelength $\lambda_{LB0}$ of the illuminating light LB0 may be modulated by varying an operating current of a semiconductor laser LS1, wherein the intensity $I_{LB0}$ of the illuminating light LB0 may vary as a function of the wavelength $\lambda$. The wavelength $\lambda_{LB0}$ of the illuminating light LB0 may be modulated by varying an operating current of a semiconductor laser LS1, wherein the intensity $I_{LB0}$, of the illuminating light LB0 may vary as a function of the operating current. The method may comprise e.g. filling the cell 200 with a (non-absorbing) reference gas, by varying the wavelength $\lambda_{LB0}$ of the illuminating light LB0, and by measuring a reference intensity function $I_0(\lambda)$ or a reference transmittance function $I_0(\lambda)/I_{LB0}$ when the cell 200 is filled with the reference gas.

A reference intensity function $I_0(\lambda)$ may be measured e.g. before and/or after measuring a spectrum of an absorbing sample GAS1. The reference intensity function $I_0(\lambda)$ may be optionally corrected e.g. by using one or more auxiliary reference intensity values $I_{0,AUX}(\lambda_0)$. The one or more auxiliary reference intensity values $I_{0,AUX}(\lambda_0)$ may be measured when the sample cell contains the absorbing sample GAS1, e.g. at a spectral position $(\lambda_0)$ where the absorbing sample GAS1 has low of negligible spectral absorbance. The reference intensity function $I_0(\lambda)$ may be optionally corrected e.g. by multiplying the reference intensity function $I_0(\lambda)$ with the ratio $I_{0,AUX}(\lambda_0)/I_0(\lambda_0)$. The correction may compensate e.g. a drift of response of the detector. A measured spectral transmittance value $I_{LB2}(\lambda)/I_0(\lambda)$ may be optionally determined e.g. by using a measured intensity value $I_{LB2}(\lambda)$, by using a reference intensity function $I_0(\lambda)$, and by using one or more auxiliary reference intensity values $I_{0,AUX}(\lambda_0)$. A corrected spectral transmittance value may be determined e.g. by multiplying a measured spectral transmittance value $I_{LB2}(\lambda)/I_0(\lambda)$ with the ratio $I_0(\lambda_0)/I_{0,AUX}(\lambda_0)$.

Light reflected back to a laser light source LS1 may disturb operation of the laser light source LS1. The scrambling sample cell 200 may reduce or eliminate a disturbing effect caused by reflection of the transmitted light LB2 from the detector DET1.

Using the scrambling sample cell 200 may reduce or eliminate a disturbing effect of temperature variations of the cell on the measured spectral data $I_{LB2}(\lambda)/I_0(\lambda)$, by reducing or eliminating disturbing interference effects.

The measuring apparatus 500 may be arranged to measure one or more spectral features of one or more substances selected from the following group: carbon dioxide $CO_2$, carbon monoxide CO, water vapor $H_2O$, methane $CH_4$, ethylene $C_2H_4$, isotope $^{18}O$ bound in $CO_2$, isotope $^{13}C$ bound in $CO_2$, isotope $^{17}O$ bound in $CO_2$, isotope $^{18}O$ bound in water vapor $H_2O$, di-deuterium monoxide $D_2O$, methane $CH_4$, ethylene $C_2H_4$, deuterium (D) bound in ethylene $C_2H_4$, isotope $^{13}C$ bound in ethylene $C_2H_4$.

For the person skilled in the art, it will be clear that modifications and variations of the devices, apparatuses, and the methods according to the present invention are perceivable. The figures are schematic. The particular embodiments described above with reference to the accompanying drawings are illustrative only and not meant to limit the scope of the invention, which is defined by the appended claims.

The invention claimed is:

1. A measuring apparatus for measuring a spectrum of a gaseous sample, the apparatus comprising:
    a tunable laser light source to provide an illuminating light beam,
    a sample cell for containing the gaseous sample, the cell comprising an inner surface to provide transmitted light by reflecting light of the illuminating light beam such that the transmitted light is transmitted through the gaseous sample, and
    a detector to detect intensity of the transmitted light guided through the sample cell,
    wherein the measuring apparatus is arranged to measure one or more spectral transmittance value of the sample by modulating the spectral position of the illuminating light, and by detecting the intensity of the transmitted light at two or more different spectral positions of the illuminating light,
    wherein the apparatus further comprises a pressure control system to maintain an absolute pressure of the gaseous sample smaller than 50 kPa inside the sample cell so as to reduce spectral widths of spectral features of the gaseous sample, wherein the total reflectance of the inner surface is greater than 80% at the wavelength of the illuminating light beam, wherein the specular reflectance of the inner surface is smaller than 50% such that the transmitted light has scrambled phase,
    wherein a longitudinal dimension of the inner surface is in the range of 10 to 100 times a minimum diameter of the inner surface, and wherein the divergence of the illuminating light beam in a transverse direction is greater than 30° so as to cause multiple consecutive reflections of the scrambled light from the inner surface.

2. The apparatus of claim 1, wherein the illuminating light beam is coupled from a laser emitter into the sample cell without using focusing and/or collimating optics between the laser emitter and the sample cell.

3. The apparatus of claim 1, wherein the illuminating light beam is coupled from a laser emitter into the sample cell such that the refractive power of optics between the laser emitter and the sample cell is smaller than 50 dioptre.

4. The apparatus according to claim 1, wherein the light source is an interband cascade laser or a quantum cascade laser.

5. The apparatus according to claim 1, wherein the apparatus is arranged to modulate the wavelength of the illuminating beam, and to measure a ratio of the concentration of carbon isotope $^{13}C$ bound in carbon dioxide to the concentration of carbon isotope $^{12}C$ bound in carbon dioxide by detecting spectral transmittance of carbon dioxide at three or more spectral positions.

6. The apparatus according to claim 1, wherein the arithmetic mean roughness Ra of the inner surface of the sample cell is in the range of 0.25 to 2 times the maximum wavelength of the spectral modulation range of the illuminating light beam.

7. The apparatus according to claim 1, wherein the wavelength of the illuminating light beam is in the range of 4.3 μm to 4.4 μm.

8. The apparatus according to claim 1, wherein the arithmetic mean roughness Ra of the inner surface of the sample cell is in the range of 0.5 μm to 8 μm.

9. A method for measuring a spectrum of a gaseous sample, comprising:
    providing an illuminating laser light beam, providing a sample cell for containing the gaseous sample, the cell comprising an inner surface,
    varying the spectral position of the illuminating light,
    detecting intensity of transmitted light,
    providing transmitted light by using the inner surface to reflect light of the illuminating light beam such that the transmitted light is transmitted through the gaseous sample, and
    detecting intensity of transmitted light guided through the sample cell at two or more spectral positions of the illuminating light,
    wherein the method comprises:
    maintaining an absolute pressure of the gaseous sample smaller than 50 kPa inside the sample cell so as to reduce spectral widths of spectral features of the gaseous sample,
    wherein the total reflectance of the inner surface is greater than 80% at the wavelength of the illuminating light beam, where the specular reflectance of the inner surface is smaller than 50% such that the transmitted light has scramble phase,
    wherein the longitudinal dimension of the inner surface is in the range of 10 to 100 times a minimum diameter of the inner surface, and wherein the divergence of the illuminating light beam in a transverse direction is greater than 30° so as to cause multiple consecutive reflections of the scrambled light from the inner surface.

* * * * *